US008993819B2

(12) United States Patent
Teles et al.

(10) Patent No.: US 8,993,819 B2
(45) Date of Patent: Mar. 31, 2015

(54) PROCESS FOR PREPARING CYCLOHEPTENE

(75) Inventors: Joaquim Henrique Teles, Waldsee (DE); Michael Limbach, Worms (DE); Richard Dehn, Ludwigshafen (DE); Stephan Deuerlein, Ludwigshafen (DE); Manuel Danz, Plankstadt (DE)

(73) Assignee: BASF SE, Ludwigshafen (DE)

( * ) Notice: Subject to any disclaimer, the term of this patent is extended or adjusted under 35 U.S.C. 154(b) by 245 days.

(21) Appl. No.: 13/545,446

(22) Filed: Jul. 10, 2012

(65) Prior Publication Data

US 2013/0018205 A1  Jan. 17, 2013

Related U.S. Application Data

(60) Provisional application No. 61/506,679, filed on Jul. 12, 2011.

(51) Int. Cl.
*C07C 6/04* (2006.01)
*C07C 13/24* (2006.01)

(52) U.S. Cl.
CPC ............... *C07C 6/04* (2013.01); *C07C 2101/18* (2013.01); *C07C 2531/22* (2013.01)
USPC ........... 585/366; 585/358; 585/367; 562/400; 562/861; 568/357; 568/420; 564/446

(58) Field of Classification Search
CPC .... C07C 6/04; C07C 2101/18; C07C 2531/22
USPC .......................................... 585/366, 367, 358
See application file for complete search history.

(56) References Cited

U.S. PATENT DOCUMENTS

| | | | |
|---|---|---|---|
| 3,109,040 A | 10/1963 | Richard J. Lee | |
| 5,077,447 A | 12/1991 | Miller et al. | |
| 5,969,170 A | 10/1999 | Grubbs et al. | |
| 6,111,121 A | 8/2000 | Grubbs et al. | |
| 6,635,768 B1 | 10/2003 | Herrmann et al. | |
| 6,759,537 B2 | 7/2004 | Grubbs et al. | |
| 6,903,241 B2 | 6/2005 | Woehrle et al. | |
| 6,921,735 B2 | 7/2005 | Hoveyda et al. | |
| 7,163,908 B2 | 1/2007 | Woehrle et al. | |
| 2005/0261451 A1 | 11/2005 | Ung et al. | |
| 2009/0258866 A1 | 10/2009 | Luo | |
| 2011/0046413 A1 | 2/2011 | Teles et al. | |
| 2011/0065939 A1 | 3/2011 | Teles et al. | |
| 2011/0137097 A1 | 6/2011 | Tschirschwitz et al. | |
| 2011/0137098 A1 | 6/2011 | Tschirschwitz et al. | |
| 2011/0218359 A1 | 9/2011 | Limbach et al. | |
| 2011/0272108 A1 | 11/2011 | Prochazka et al. | |
| 2011/0275868 A1 | 11/2011 | Prochazka et al. | |
| 2011/0275869 A1 | 11/2011 | Prochazka et al. | |
| 2011/0319657 A1 | 12/2011 | Schneider et al. | |
| 2012/0058463 A1 | 3/2012 | Deuerlein et al. | |
| 2012/0087851 A1 | 4/2012 | Deuerlein et al. | |
| 2012/0088935 A1 | 4/2012 | Schelper et al. | |
| 2012/0101306 A1 | 4/2012 | Lanver et al. | |
| 2012/0101307 A1 | 4/2012 | Lanver et al. | |
| 2012/0123136 A1 | 5/2012 | Miller et al. | |
| 2012/0132032 A1 | 5/2012 | Domke et al. | |
| 2012/0142950 A1 | 6/2012 | Teles et al. | |
| 2012/0165588 A1 | 6/2012 | Dehn et al. | |

FOREIGN PATENT DOCUMENTS

| | | |
|---|---|---|
| DE | 10 2008 008 299 B3 | 8/2009 |
| EP | 0 632 004 A1 | 1/1995 |
| EP | 0 993 465 | 4/2000 |
| EP | 1 288 181 | 3/2003 |
| EP | 1 468 004 | 10/2004 |
| WO | WO 01/05738 A1 | 1/2001 |
| WO | WO 2007/003135 A1 | 1/2007 |
| WO | WO 2008/065187 A1 | 6/2008 |
| WO | WO 2011/006990 A1 | 1/2011 |
| WO | WO 2011/020878 A2 | 2/2011 |
| WO | WO 2011/051374 A1 | 5/2011 |
| WO | WO 2011/069929 A1 | 6/2011 |
| WO | WO 2011/069957 A1 | 6/2011 |
| WO | WO 2011/107559 A2 | 9/2011 |
| WO | WO 2011/138355 A2 | 11/2011 |
| WO | WO 2011/138356 A1 | 11/2011 |
| WO | WO 2011/138357 A1 | 11/2011 |

(Continued)

OTHER PUBLICATIONS

Denmark et al, Tetrahedron, 60, (2004), p. 9695-9708.*

(Continued)

*Primary Examiner* — Yong Chu
(74) *Attorney, Agent, or Firm* — Oblon, McClelland, Maier & Neustadt, L.L.P.

(57) ABSTRACT

The present invention provides a process for preparing cycloheptene and derivatives thereof by ring-closing metathesis of unsymmetric 1,8-dienes whose C—C double bond at the 8 position is nonterminal. Cycloheptene and the cycloheptanone, cycloheptylamine, cycloheptanecarbaldehyde, cycloheptanecarboxylic acid and cycloheptanecarbonyl chloride conversion products thereof, and the derivatives thereof, are important synthesis units for active ingredient compounds. The ring-closing metathesis is preferably performed as a reactive distillation. The unsymmetric 1,8-dienes for the ring-closing metathesis can be obtained by catalytic decarbonylation or oxidative decarboxylation from the corresponding unsaturated carboxylic acids or carboxylic acid derivatives.

15 Claims, No Drawings

(56) References Cited

FOREIGN PATENT DOCUMENTS

| WO | WO 2012/000964 A1 | 1/2012 |
|---|---|---|
| WO | WO 2012/028701 A2 | 3/2012 |
| WO | WO 2012/045786 A1 | 4/2012 |
| WO | WO 2012/049611 A1 | 4/2012 |
| WO | WO 2012/055716 A2 | 5/2012 |
| WO | WO 2012/055754 A2 | 5/2012 |
| WO | WO 2012/065879 A1 | 5/2012 |
| WO | WO 2012/072615 A1 | 6/2012 |
| WO | WO 2012/076543 A1 | 6/2012 |
| WO | WO 2012/084673 A1 | 6/2012 |

OTHER PUBLICATIONS

Yeh et al, Bioorganic & Medicinal Chemistry Letters, 16, (2006), p. 5408-5413.*
International Search Report issued Oct. 19, 2012 in PCT/EP2012/062944.
Ian W. Ashworth et al., "On the Relationship Between Structure and Reaction Rate in Olefin Ring-Closing Metathesis", Chemical Communications, vol. 46, XP-002684624, 2010, pp. 7145-7147.
Scott E. Denmark et al., "Sequential Ring-Closing Metathesis/Pd-catalyzed, Si-assisted Cross-coupling Reactions: General Synthesis of Highly Substituted Unsaturated Alcohols and Medium-sized Rings Containing a 1,3-cis-cis Diene Unit", Tetrahedron, Elsevier Science Publishers, vol. 60, No. 43, XP-004573966, Oct. 18, 2004, pp. 9695-9708.
Vince S.C.Yeh et al.,"Synthesis and Structural Activity Relationship of 11β-HSD1 Inhibitors with Novel Adamantane Replacements", Bioorganic & Medicinal Chemistry Letters, vol. 16, XP-002684625, 2006, pp. 5408-5413.
U.S. Appl. No. 13/503,548, filed Apr. 23, 2012, Kevin Mueller, et al.
U.S. Appl. No. 13/434,176, filed Mar. 29, 2012, Stephan Deuerlein, et al.
U.S. Appl. No. 13/479,961, filed May 24, 2012, Eckhard Stroefer, et al.
Amos Ben-Asuly et al., "A Thermally Switchable Latent Ruthenium Olefin Metathesis Catalyst", Organometallics, 2008, vol. 27, pp. 811-813.
Jay C. Conrad et al., "Ruthenium-Catalyzed Ring-Closing Metathesis: Recent Advances, Limitations and Opportunities", Current Organic Chemistry, 2006, vol. 10, pp. 185-202.
Jochanan Blum et al., "Decarbonylation of Aromatic Carbonyl Compounds Catalyzed by Rhodium Complexes", Journal of the American Chemical Society, May 10, 1967, vol. 89, No. 10, pp. 2338-2341.
Kiyotaka Ohno et al., "Organic Syntheses by Means of Noble Metal Compounds. XXXV. Novel Decarbonylation Reactions of Aldehydes and Acyl Halides Using Rhodium Complexes", Journal of the American Chemical Society, Jan. 3, 1968, vol. 90, No. 1, pp. 99-107.
Jiro Tsuji et al., "Decarbonylation Reactions Using Transition Metal Compounds", Synthesis, Dec. 1969, pp. 157-169.
Lukas J. Goossen et al., "A mild and efficient protocol for the conversion of carboxylic acids to olefins by a catalytic decarbonylative elimination reaction", Chem. Commun., 2004, pp. 724-725.
Joseph A. Miller et al., "A Highly Catalytic and Selective Conversion of Carboxylic Acids to 1-Alkenes of One Less Carbon Atom", J. Org. Chem., 1993, vol. 58, pp. 18-20.
Thomas A. Kirkland et al., "Effects of Olefin Substitution on the Ring-Closing Metathesis of Dienes", J. Org. Chem., 1997, vol. 62, pp. 7310-7318.
Janis Louie et al., "Tandem Catalysis: The Sequential Mediation of Olefin Metathesis, Hydrogenation, and Hydrogen Transfer with Single-Component Ru Complexes", J. Am. Chem. Soc., 2001, vol. 123, pp. 11312-11313.
Choon Woo Lee et al., "Formation of Macrocycles via Ring-Closing Olefin Metathesis", J. Org. Chem., 2001, vol. 66, pp. 7155-7158.
Maier, "Synthesis of Medium-Sized Rings by the Ring-Closing Metathesis Reaction", Angew. Chem. Int. Ed., 2000, vol. 39, No. 12, pp. 2073-2077.
Grubbs, "Ring-Closing Metathesis and Related Processes in Organic Synthesis", *Chem. Res.*, 1995, vol . 28, No. 11, pp. 446-452.
Ghosh et al, "Factors influencing ring closure through olefin metathesis—A perspective", *J. Chem. Sci.*, 2006, vol. 118, No. 3, pp. 223-235.
Fuerstner, "Recent advancements in ring closing olefin metathesis", *Topics in Catalysis*, 1997, vol. 4, pp. 285-299.

* cited by examiner

PROCESS FOR PREPARING CYCLOHEPTENE

DESCRIPTION

The present application incorporates provisional U.S. application 61/506, 679, filed Jul. 12, 2011, by reference.

The present invention relates to a process for preparing cycloheptene by ring-closing metathesis of 1,8-dienes whose C—C double bond at the 8 position is nonterminal. It further relates to processes for preparing the cycloheptanone, cycloheptylamine, cycloheptanecarbaldehyde, cycloheptanecarboxylic acid and cycloheptanecarbonyl chloride conversion products from the cycloheptene prepared in accordance with the invention. In an analogous manner, the invention also relates to processes for preparing the corresponding derivatives substituted by one or more radicals on the cycloheptene ring.

Compounds having a cycloheptane ring are very often used as active ingredients. Market maturity has been attained, for example, by bencyclan (Fludilat®) as a calcium channel blocker, heptabarbital (Medomin®) as a barbiturate with action for a moderate period, and incadronic acid (Bisphonal®) to counteract malignant hypercalcemia.

All these active ingredients are synthesized proceeding from cycloheptanone or from cycloheptylamine. Many other active ingredients described in the literature are synthesized proceeding from other cycloheptane derivatives. Those of significance include cycloheptanecarbaldehyde and cycloheptanecarboxylic acid, which is readily preparable therefrom, and cycloheptanecarbonyl chloride. However, only cycloheptanone (suberone) is obtainable industrially to date via a relatively long and complex synthesis route.

EP 0 632 004 describes the synthesis of cycloheptanone by cyclization of suberonitrile at high temperature in the presence of water over an Si/Ti mixed oxide catalyst. The yield is relatively good at 85% but the service life of the catalyst is only moderate. Suberonitrile has to be prepared in a multistage synthesis: proceeding from 1,6-hexanediol, which is converted to 1,6-dichlorohexane with phosgene, and then reacted with NaCN, or proceeding from suberic acid via suberamide with subsequent elimination of water with $P_4O_{10}$. Both routes are very long and offer only one way of obtaining cycloheptanone.

A synthesis of all abovementioned starting units (cycloheptanone, cycloheptylamine, cycloheptanecarbaldehyde, cycloheptanecarboxylic acid and cycloheptanecarbonyl chloride) can be effected much more simply proceeding from cycloheptene as the central unit:

Cycloheptene can be prepared by ring-closing metathesis (RCM) proceeding from the α,ω-olefin 1,8-nonadiene which cyclizes by its two terminal C—C double bonds to eliminate volatile ethene (Ben-Asuly et al., Organometallics (2008), 27:811-813). Disadvantages are particularly the lack of industrial availability of the reactant and the relatively high dilution. The preparation of cycloheptene or derivatives thereof by ring-closing metathesis proceeding from unsymmetric α,ω-olefins or even from dienes with only one terminal C—C double bond is not described in the literature. Instead, it is assumed in the literature that, in the case of use of unsymmetric dienes, dimerization by acyclic diene metathesis (ADMET) is preferred (Conrad & Fogg, Curr Org Chemistry (2006), 10:185-202).

At present, there exists no simple industrial route to cycloheptene. Such a route proceeding from industrially readily available starting materials would thus be desirable.

The object underlying the invention can therefore be considered that of providing a process for preparing cycloheptene which proceeds from alternative, especially from industrially readily available, starting materials.

Accordingly, the present invention relates to a process for preparing cycloheptene or derivatives thereof by catalytic ring-closing metathesis of 1,8-dienes of the formula I

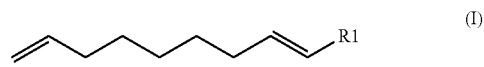

and derivatives thereof, where R1 is an alkyl group having 1 to 20 carbon atoms, especially having 4, 6, 8 or 10 carbon atoms. The present invention preferably relates to a process for preparing cycloheptene by catalytic ring-closing metathesis of 1,8-dienes of the formula I where R1 is an alkyl group having 1 to 20 carbon atoms, especially having 4, 6, 8 or 10 carbon atoms. The 1,8-dienes of the formula I or derivatives thereof preferably do not have any conjugated double bonds. The 1,8-diene of the formula I is preferably heptadeca-1,8-diene.

Alkyl groups in the context of the invention are aliphatic hydrocarbon radicals without heteroatoms. They may be branched or unbranched and saturated or unsaturated. They are preferably saturated and unbranched.

Derivatives of the 1,8-dienes of the formula I are those compounds which have been modified independently by one or more, preferably by 1 to 3, R2 substituents at positions 2 to 7 proceeding from the 1,8-dienes of the formula I. R2 is an alkyl group having 1 to 4 carbon atoms, an alkoxy group

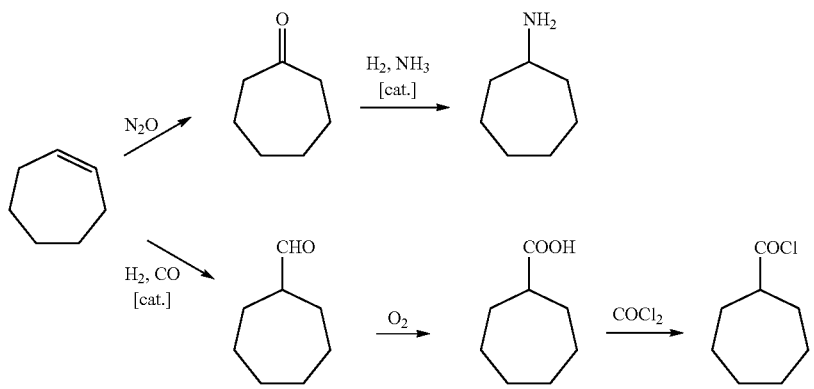

having 1 to 4 carbon atoms, a phenyl group, a halide, preferably chloride or bromide, an amino group, a hydroxyl group or a sulfo group.

In principle, all conceivable metathesis catalysts can be used for the ring-closing metathesis of the 1,8-dienes of the formula I or derivatives thereof. Since the reaction has a positive activation entropy (two molecules are obtained from one), the reaction is favored at higher temperatures. Therefore, for this reaction, it is also possible to employ conventional heterogeneous catalysts for the high-temperature gas phase metathesis, for example $WO_3/SiO_2$ catalysts. The heterogeneous catalysts used are, for example, not only $WO_3/SiO_2$ but also $Re_2O_7/Al_2O_3$ catalysts. The homogeneous metathesis catalysts used are typically salts or complexes of tungsten or of rhenium (e.g. $WCl_6$ or $CH_3Re(CO)_5$) or metal-carbene complexes based on ruthenium or molybdenum (first generation Grubbs catalyst, second generation Grubbs catalyst, Schrock catalyst, Hoveyda-Grubbs catalyst). The catalysts based on Re, Mo or W are frequently used in combination with a cocatalyst (usually organometallic complexes of main group elements such as aluminum alkyls, aluminum alkyl chlorides or zinc alkyls) and an activator (for example oxygen compounds such as ethanol or diethyl ether). Suitable metathesis catalysts are described in the literature (for example U.S. Pat. Nos. 5,969,170, 6,111,121, 6,921,735, U.S. Ser. No. 11/094,102, U.S. Pat. No. 6,759,537, EP 993465, U.S. Pat. No. 6,635,768, WO 2007/003135, WO 2008/065187, EP1468004, DE102008008299). Suitable metathesis catalysts are ruthenium-carbene complexes, for example dichloro(3-methyl-2-butenylidene)bis(tricyclopentylphosphine)-ruthenium(II), isopentenylidene(1,3-dimesitylimidazolidin-2-ylidene) (tricyclohexylphosphine)-ruthenium(II) dichloride, benzylidenebis(tricyclohexylphosphine)dichlororuthenium, 1,3-bis(2,4,6-trimethylphenyl)-2-(imidazolidinylidene)dichloro(phenylmethylene)-(tricyclohexylphosphine)ruthenium, dichloro(o-isopropoxyphenylmethylene)(tricyclohexylphosphine)ruthenium(II), (1,3-bis(2,4,6-trimethylphenyl)-2-imidazolidinylidene)dichloro(o-isopropoxyphenylmethylene)ruthenium, 1,3-bis(2-methylphenyl)-2-imidazolidinylidene]-dichloro(phenylmethylene)(tricyclohexylphosphine)ruthenium(II), dichloro[1,3-bis(2-methylphenyl)-2-imidazolidinylidene](2-isopropoxyphenylmethylene)ruthenium(II), dichloro[1,3-bis(2,4,6-trimethylphenyl)-2-imidazolidinylidene][3-(2-pyridinyl)propylidene]ruthenium(II), dichloro[1,3-bis(2,4,6-trimethylphenyl)-2-imidazolidinylidene](benzylidene)bis(3-bromopyridine)ruthenium(II), [1,3-bis(2,6-di-i-propylphenyl)-4,5-dihydroimidazol-2-ylidene]-[2-i-propoxy-5-(trifluoroacetamido)phenyl]methyleneruthenium(II) dichloride, bis(tricyclohexylphosphine)-3-phenyl-1H-inden-1-ylidene-ruthenium(II) dichloride, bis(tricyclohexylphosphine)[(phenylthio)methylene]ruthenium(II) dichloride, bis(tricyclohexylphosphine)[(phenylthio)methylene]ruthenium(II) dichloride, 1,3-bis(2,4,6-trimethylphenyl)-4,5-dihydroimidazol-2-ylidene[2-(i-propoxy)-5-(N,N-dimethylaminosulfonyl)phenyl] methylene ruthenium(II) dichloride, 1,3-bis(2,4,6-trimethylphenyl)-4,5-dihydroimidazol-2-ylidene[2-(i-propoxy)-5-(N,N-dimethylaminosulfonyl)phenyl]methyleneruthenium(II) dichloride, [1,3-bis(2,4,6-trimethylphenyl)-2-imidazolidinylidene]-2-[[(4-methylphenyl)imino]methyl]-4-nitrophenolyl]-[3-phenyl-1H-inden-1-ylidene]ruthenium(II) chloride; [1,3-bis(2,4,6-trimethylphenyl)-2-imidazolidinylidene]-2-[[(2-methylphenyl)imino]-methyl]phenolyl[-]3-phenyl-1H-inden-1-ylidene]ruthenium(II) chloride, 3-phenyl-1H-inden-1-ylidene[bis(i-butylphobane)]ruthenium(II) dichloride, {[2-(i-propoxy)-5-(N,N-dimethylaminosulfonyl)phenyl] methylene}(tricyclohexylphosphine)ruthenium(II) dichloride, tricyclohexylphosphine [1,3-bis(2,4,6-trimethylphenyl)-4,5-dihydroimidazol-2-ylidene]-[(phenylthio)methylene]ruthenium(II) dichloride, tricyclohexylphosphine[1,3-bis(2,4,6-trimethylphenyl)imidazol-2-ylidene][3-phenyl-1H-inden-1-ylidene]ruthenium(II) dichloride, tricyclohexylphosphine[1,3-bis(2,4,6-trimethylphenyl)imidazol-2-ylidene][2-thienylmethylene]ruthenium(II) dichloride, tricyclohexylphosphine[2,4-dihydro-2,4,5-triphenyl-3H-1,2,4-triazol-3-ylidene][2-thienylmethylene]ruthenium(II) dichloride, tricyclohexylphosphine[4,5-dimethyl-1,3-bis(2,4,6-trimethylphenyl)imidazol-2-ylidene][2-thienylmethylene]ruthenium(II) dichloride, tricyclohexylphosphine[3-phenyl-1H-inden-1-ylidene][1,3-bis(2,4,6-trimethylphenyl)-4,5-dihydroimidazol-2-ylidene] ruthenium(II) dichloride, trifluoroacetato[4,5-dihydro-1,3-bis(2,4,6-trimethylphenyl)imidazol-2-ylidene]tetra(2,2-dimethylpropanenitrile)ruthenium(II) trifluoroacetate or tri(i-propoxy)phosphine(3-phenyl-1H-inden-1-ylidene)[1,3-bis(2,4,6-trimethylphenyl)-4,5-dihydroimidazol-2-ylidene] ruthenium(II) dichloride.

Depending on the catalyst type used, the reaction is performed at mild temperatures (for example 0 to 100° C.) or at elevated temperature (for example 100 to 500° C.).

The catalytic ring-closing metathesis can be effected in the liquid phase or in the gas phase. It can be performed either in the form of homogeneous catalysis or in the form of heterogeneous catalysis.

For the inventive ring-closing metathesis, preference is given to using Ru catalysts, for example the Ru catalysts of the formulae II (Mes=mesityl, Ph=phenyl, Pr=propyl), III (where Cy=cyclohexyl, Ph=phenyl) or IV (2nd generation Hoveyda-Grubbs catalyst where Mes=mesityl)

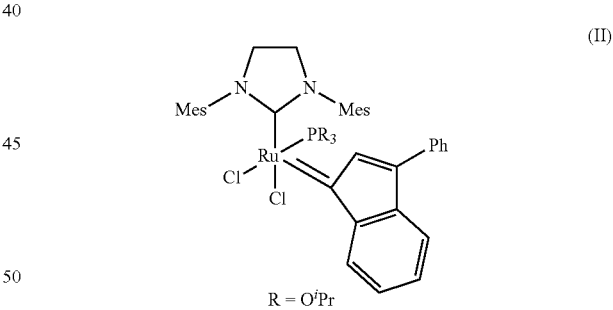

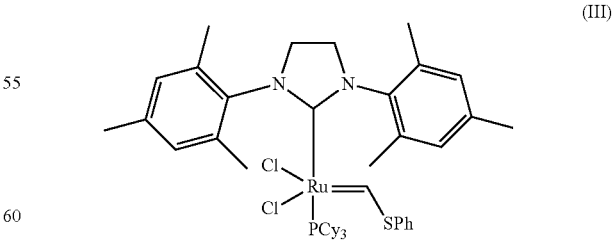

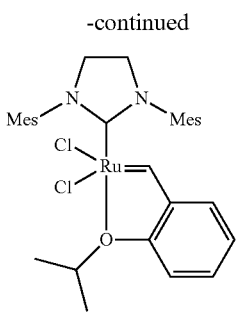 (IV)

In the ring-closing metathesis of 1,8-dienes of the formula I or derivative thereof, cycloheptene or derivative thereof is formed with elimination of an olefin of the formula V

 (V)

as a by-product. This by-product can dimerize under the reaction conditions with elimination of ethene to form the olefin of the formula VI

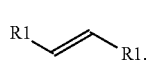 (VI)

In the case of the ring-closing metathesis of heptadeca-1,8-diene, the eliminated by-product of the formula V is 1-decene and the corresponding dimerization product of the formula VI is 9-octadecene. The olefins of the formulae V and VI, and especially 1-decene and 9-octadecene, are likewise industrially important products of value which can be isolated from the reaction mixture. The olefins of the formula VI, for example 9-octadecene, are typically obtained as the bottom product in the inventive ring-closing metathesis reaction. The olefins of the formulae V and VI can be obtained in a coproduction in addition to the cycloheptene or derivative thereof in the process according to the invention.

The inventive ring-closing metathesis can be performed in batchwise, semibatchwise or continuous mode. Preference is given to performing the inventive ring-closing metathesis as a reactive distillation.

In the case of performance of the inventive ring-closing metathesis in batchwise mode, the reactant (1,8-diene of the formula I or a derivative thereof) and the metathesis catalyst are initially charged, preferably in an inert solvent, and exposed to the reaction conditions. The reaction is effected preferably at a temperature of 0 to 500° C., more preferably of 20 to 100° C., and under a pressure of preferably 1 to 5 bar, more preferably under standard pressure. The pressure should be selected such that it is greater than the vapor pressure of the reaction mixture at the appropriate temperature. The reactant is preferably initially charged in a concentration of not more than 1.0 mol/l, preferably not more than 0.5 mol/l, for example in a concentration range from 0.01 to 0.1 mol/l. The solvent is preferably selected such that it can be removed easily from the cycloheptene reaction product or derivative thereof, i.e., for example in the case of a distillative removal, has a sufficiently different boiling point. The boiling point of the solvent preferably differs from that of cycloheptene or derivative thereof within the pressure range between 5 and 1500 mbar by at least 20° C., more preferably by at least 50° C. The solvent preferably has a higher boiling point than cycloheptene or the derivative thereof. The solvent preferably does not form any azeotropes with the cycloheptene or derivative thereof. Suitable solvents are, for example, diphenyl ether, dichlorobenzene, dichloroethane, xylene, cymene, toluene and dichloromethane. The amount of the metathesis catalyst used is preferably not more than 0.1 mol %, more preferably not more than 0.05 mol %, based on the reactant. The optimal duration of the reaction may be different for the particular reaction and the particular reaction conditions. It can be determined by taking samples from the reaction mixture and analyzing the product content. Typically, the reaction time is 0.5 to 48 h, preferably 1 to 6 h. In the case of too short a reaction time, the product yield is suboptimal due to incomplete conversion of the reactants, and in the case of too long a reaction time due to unwanted side reactions or further reactions of the product.

In the case of performance of the inventive ring-closing metathesis as a reactive distillation in batchwise mode, the reactant (1,8-diene of the formula I or a derivative thereof) and the metathesis catalyst are initially charged, preferably in an inert solvent, and exposed to the reaction conditions. The reaction is effected preferably at a temperature of 0 to 500° C., more preferably of 20 to 100° C., and under a pressure of preferably 1 to 150 mbar, more preferably of 5 to 100 mbar. The pressure should be selected such that the vapor pressure of the cycloheptene reaction product or derivative thereof at the appropriate temperature is greater than the liquid phase pressure applied, such that the product can be removed by distillation during the reaction. The reactant is preferably initially charged in a concentration of not more than 2 mol/l, preferably not more than 1 mol/l, for example within a concentration range from 0.01 to 0.5 mol/l. The solvent is preferably selected such that it evaporates only slightly (less than 10% of the volume originally used during the overall reaction), if at all, during the reaction under the selected reaction conditions. The boiling point of the solvent within the pressure range between 5 and 1500 mbar is preferably at least 20° C., more preferably at least 50° C., higher than that of cycloheptene or derivative thereof. The solvent preferably does not form any azeotropes with the cycloheptene or derivative thereof. Suitable solvents are, for example, high-boiling aromatic hydrocarbons such as xylene, toluene or cymene, halogenated hydrocarbons such as dichloromethane or dichloroethane, halogenated aromatics such as dichlorobenzenes and diphenyl ether. The amount of the metathesis catalyst used is preferably not more than 0.1 mol %, more preferably not more than 0.05 mol %, based on the reactant. The optimal duration of the reaction may be different for the particular reaction and the particular reaction conditions. It can be determined by taking samples from the reaction mixture and analyzing the conversion of the reactant. The reaction time is typically 0.5 to 48 h, preferably 1 to 6 h. In the case of too short a reaction time, the product yield is suboptimal due to incomplete conversion of the reactants; too long a reaction time is uneconomic. The reaction mixture preferably comprises an entraining agent which improves the distillative removal of the product during the reaction. The entraining agent is preferably selected such that it has a similar boiling point to the product (plus/minus 20° C., preferably plus/minus 10° C., at the pressure under which the reaction or distillation is performed). A suitable entraining agent is toluene. The entraining agent is preferably separated from the product after the distillative removal and sent back to the reaction mixture. Alternatively, it is also possible to continuously add fresh entraining agent to the reaction mixture. In the case of this mode of operation as a reactive distillation, the product formed is removed from the reaction mixture directly during the reaction and thus protected from unwanted side reactions.

In the case of performance of the inventive ring-closing methathesis as a reactive distillation in semibatchwise mode, the metathesis catalyst is initially charged in an inert solvent. Under reaction conditions, the reactant (1,8-diene of the formula I or a derivative thereof) is metered in. The reaction is effected preferably at a temperature of 0 to 500° C., more preferably of 20 to 100° C., and under a pressure of preferably 1 to 200 mbar, more preferably 5 to 150 mbar. The pressure should be selected such that the vapor pressure of the cycloheptene reaction product or derivative thereof at the appropriate temperature is greater than the liquid phase pressure applied, such that the product can be removed by distillation during the reaction. The reactant is preferably metered in at such a flow rate that the concentration of the reactant does not exceed a value of not more than 1 mol/l, preferably not more than 0.5 mol/l, and is, for example, within a concentration range from 0.005 to 0.5 mol/l, preferably from 0.01 to 0.1 mol/l. The solvent is preferably selected such that it evaporates only slightly (less than 10% of the volume originally used during the overall reaction), if at all, during the reaction under the selected reaction conditions. The boiling point of the solvent within the pressure range between 5 and 1500 mbar is preferably higher by at least 20° C., more preferably by at least 50° C., than that of cycloheptene or derivative thereof. The solvent preferably does not form any azeotropes with the cycloheptene or derivative thereof. Suitable solvents are, for example, high-boiling aromatic hydrocarbons such as xylene, toluene or cymene, halogenated hydrocarbons such as dichloromethane or dichloroethane, halogenated aromatics such as dichlorobenzenes and diphenyl ether. The amount of the metathesis catalyst used is preferably not more than 0.1 mol %, more preferably not more than 0.05 mol %, based on the reactant. The reaction mixture preferably comprises an entraining agent which improves the distillative removal of the product during the reaction. The entraining agent is preferably selected such that it has a similar boiling point to the product (plus/minus 20° C., preferably plus/minus 10° C., at the pressure under which the reaction or distillation is performed). A suitable entraining agent is toluene. The entraining agent is preferably separated from the product after the distillative removal and sent back to the reaction mixture. Alternatively, it is also possible to continuously add fresh entraining agent to the reaction mixture. In the case of this mode of operation as a reactive distillation, the product formed is removed constantly from the reaction mixture directly during the reaction, and hence protected from unwanted side reactions. The reactive distillation in semibatchwise mode allows a high conversion with comparatively low reactant concentration in the reaction mixture, which allows intermolecular side reactions, for example the dimerization of the 1,8-diene of the formula I or derivatives thereof, to be additionally suppressed.

In the case of performance of the inventive ring-closing methathesis as a continuous reactive distillation, the reactant (1,8-diene of the formula I or a derivative thereof) is supplied, preferably in an inert solvent, continuously to the reactive zone of a rectification column with rectifying and stripping sections. The reactive zone is initially charged with the methathesis catalyst. The reaction is effected preferably at a temperature of 0 to 500° C., more preferably of 20 to 100° C., and under a pressure of preferably 1 to 200 mbar, more preferably of 5 to 150 mbar. The products (cycloheptene or derivatives thereof and the olefins eliminated in the metathesis or dimers thereof) are removed from the reaction mixture by distillation in the rectification column and drawn off continuously. Preference is given to selecting a solvent having a boiling point which enables the solvents to very substantially remain in the reactive zone of the column. Solvent drawn off from the column with the products is preferably removed from the products (for example by distillation) and fed back to the reaction together with the reactant. The reaction conditions are preferably adjusted such that the concentration of the reactant in the reactive zone does not exceed a value of not more than 1 mol/l, preferably not more than 0.5 mol/l, and is, for example, within a concentration range from 0.005 to 0.5 mol/l, preferably from 0.01 to 0.1 mol/l. Suitable solvents are, for example, high-boiling aromatic hydrocarbons such as xylene, toluene or cymene, halogenated hydrocarbons such as dichloromethane or dichloroethane, halogenated aromatics such as dichlorobenzenes and diphenyl ether. The amount of the metathesis catalyst used is preferably not more than 0.1 mol %, more preferably not more than 0.05 mol %, based on the reactant. Preference is given to adding an entraining agent to the reaction mixture, which improves the distillative removal of the product during the reaction. The entraining agent is preferably separated from the product after the distillative removal and sent back to the reaction mixture.

The 1,8-diene of the formula I for the inventive catalytic ring-closing metathesis can be prepared by catalytic decarbonylation (Trost & Fleming (Eds.), Comprehensive Organic Synthesis, 1st. Ed., Elsevier (1991) 3:1040-1042) or decarboxylation (Carey & Sundberg, Advanced Organic Chemistry, Plenum Press (1990), 3rd. Ed., New York, p. 649-651) of a carboxylic acid, or of a carboxylic acid derivative of the formula VII

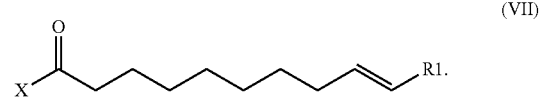

(VII)

X is a halide, preferably chloride, a hydrogen atom, an OH group or another suitable leaving group, for example an acyl group, preferably acetyl, pivaloyl or benzoyl. In principle, other carboxylic acid activations such as imidazolides or active esters are also possible. Derivatives of the 1,8-dienes of the formula I can be prepared in an analogous manner proceeding from the corresponding derivatives of the carboxylic acid or carboxylic acid derivatives of the formula VII. Heptadeca-1,8-diene can be prepared, for example, by catalytic decarbonylation or oxidative decarboxylation of oleic acid or of an oleic acid derivative, such as oleyl chloride. In a corresponding manner, a 1,8-diene of the formula I suitable for the ring-closing metathesis to give cycloheptene can also be prepared, for example, by catalytic decarbonylation or oxidative decarboxylation of myristoleic acid, palmitoleic acid, elaidic acid or gadoleic acid, or acid derivatives thereof. The corresponding use of polyunsaturated carboxylic acids or carboxylic acid derivatives, for example linoleic acid, is also possible, but ring-closing metathesis can in principle lead to unsaturated cycloaliphatics with greater ring sizes as a by-product.

Such catalytic decarbonylations or oxidative decarboxylations have already been described in principle in the literature (Blum et al., J Am Chem Soc (1967) 89:2338-2341; Ohno & Tsuji, J Am Chem Soc (1968) 90:99-107; Tsuji & Ohno, Synthesis (1969) 157-169). Goossen & Rodríguez (Chem Comm (2004) 724-725) describe, for example, the conversion of oleic acid to heptadeca-1,8-diene in the presence of an excess of pivalic anhydride and of a Pd catalyst with a yield of 69%. Likewise known is the decarbonylation of oleic acid in the presence of an excess of acetic anhydride and $PdCl_2(PPh_3)_2$ as a catalyst (Miller et al., J Org Chem (1993) 58:18-20). The same reaction with a similar catalyst system has already been described in U.S. Pat. No. 5,077,447 and in U.S. Pat. No. 3,109,040.

Carboxylic acids of the formula VII where X=OH, for example oleic acid, are converted in the catalytic decarbonylation or oxidative decarboxylation with elimination of CO and water to 1,8-dienes of the formula I, for example heptadeca-1,8-diene. Since water in this conversion is a poor leaving group, the carboxylic acids of the formula VII where X=OH are not particularly good substrates for this conversion. Advantageously, the carboxylic acid of the formula VII where X=OH is activated in situ, for example by forming a mixed anhydride with acetic anhydride or pivalic anhydride, or a carboxylic acid derivative with a better leaving group is used, for example an acid chloride. The reaction can then be regarded as a retro-Koch carbonylation. Instead of the acid, it is also possible to use the aldehyde, in which case CO and $H_2$ are eliminated and the reaction can be regarded as retro-hydroformylation. It is possible to use pure carboxylic acids or carboxylic acid derivatives of the formula VII, or else mixtures which comprise them. Such mixtures comprise the carboxylic acids or carboxylic acid derivatives of the formula VII preferably in a proportion of at least 50% by weight.

Since oleic acid and oleyl chloride are industrially available, the use thereof for the preparation of heptadeca-1,8-diene is particularly preferred.

For the catalytic decarbonylation or oxidative decarboxylation of carboxylic acids, or carboxylic acid derivatives of the formula VII, it is possible to use all catalysts described in the literature. Particular preference is given to using Pd(II) and Rh(I) complexes as catalysts.

The catalytic decarbonylation or oxidative decarboxylation of carboxylic acids, or carboxylic acid derivatives of the formula VII, to give 1,8-dienes of the formula I is effected preferably as a reactive distillation in semibatchwise mode, in which case the carboxylic acid or the carboxylic acid derivative of the formula VII is metered homogeneously into the reactor and the volatile products are removed very rapidly. In order to accomplish this, the reaction temperature is selected according to the catalyst such that a suitable reaction rate is obtained. According to this reaction temperature, the pressure is then selected such that the boiling point of the 1,8-diene of the formula I is at least 10° C. below the reaction temperature at this pressure. The reaction can be performed either in substance or in the presence of a high-boiling solvent which is inert under the reaction conditions. A "high-boiling solvent" in this context is understood to mean a solvent whose boiling temperature under the given reaction conditions is higher than the reaction temperature selected.

In a preferred variant of the catalytic decarbonylation or oxidative decarboxylation, the catalyst is first dissolved in a high-boiling solvent or an ionic liquid and this solution is applied to a porous inert support. The catalyst is then used in fixed bed reactor.

Before use in the inventive ring-closing metathesis, the 1,8-diene of the formula I is preferably purified. The purification may also be multistage. For example, proceeding from oleyl chloride, the gaseous reaction output can first be condensed, then the aqueous HCl formed can be removed by phase separation, then the organic phase can be washed with water and/or a dilute alkali, optionally also more than once, and finally the organic phase can be purified by distillation.

The cycloheptene prepared in accordance with the invention can, in a further step, for example be oxidized by means of $N_2O$ to give cycloheptanone. Also possible is a two-stage sequence of epoxidation and rearrangement of the epoxide to give suberone. The cycloheptanone in turn can be converted catalytically in a subsequent step, for example by means of hydrogen and ammonia, to give cycloheptylamine (reductive amination). Alternatively, the cycloheptene prepared in accordance with the invention can also, for example, be converted catalytically by means of hydrogen and carbon monoxide to cycloheptanecarbaldehyde (hydroformylation). This can be oxidized in a subsequent step, for example with addition of oxygen, to give cycloheptanecarboxylic acid. Cycloheptanecarboxylic acid can also be prepared directly from cycloheptene, for example according to WO 01/05738 by reaction with formic acid. The cycloheptanecarboxylic acid in turn can, for example, be converted by means of phosgene to cycloheptanecarbonyl chloride. In an analogous manner, the corresponding derivatives of cycloheptanone, of cycloheptylamine, of cycloheptanecarbaldehyde, of cycloheptanecarboxylic acid or of cycloheptanecarbonyl chloride can also be prepared proceeding from the corresponding derivative of cycloheptene with one or more R2 substituents on the cycloheptene ring, in which case this results in accordance with the invention from those compounds which have been modified independently by one or more, preferably 1 to 3, R2 substituents at positions 2 to 7 proceeding from the 1,8-dienes of the formula I. R2 is an alkyl group having 1 to 4 carbon atoms, an alkoxy group having 1 to 4 carbon atoms, a phenyl group, a halide, preferably chloride or bromide, an amino group, a hydroxyl group or a sulfo group.

The invention will now be illustrated in detail by the non-limiting examples which follow.

EXAMPLE 1

A solution of the Ru complex of the formula II (73 mg, 80 µmol) as a metathesis catalyst in diphenyl ether (222 g) was heated to 85° C. under reduced pressure (8 mbar). A solution of 1,8-heptadecadiene (21.9 g, purity 90% by weight, 83 mmol) in toluene (22 ml) was homogeneously added dropwise to this mixture by means of a syringe pump over a period of 4 h, while the cycloheptene product and other low boilers (for example 1-decene and toluene) were constantly distilled off into a receiver. At the end of the reaction, complete conversion of the reactant was detected. The amount of cycloheptene in the distillate was determined by means of GC analysis and corresponded to 4.80 g (50 mmol, 60% of the theoretical yield).

EXAMPLE 2

The reaction was performed analogously to example 1, except using 74.3 mg (83 µmol) of the Ru complex of the formula III as a metathesis catalyst. In this case too, the reactant was converted fully. The distillate comprised 4.97 g (52 mmol) of cycloheptene, corresponding to 63% of the theoretical yield.

EXAMPLE 3

The reaction was performed analogously to example 1, except using only 36.6 mg (42 µmol) of the Ru complex of the formula II. In this case too, the complete conversion of the reactant was detected at the end of the reaction. The distillate comprised 4.23 g (44 mmol) of cycloheptene, corresponding to 53% of the theoretical yield.

EXAMPLE 4

The reaction was performed analogously to example 1, except using 47.7 mg (76 µmol) of the Ru complex of the formula IV as a metathesis catalyst. In this case too, the reactant was converted fully. The distillate comprised 5.57 g (58 mmol) of cycloheptene, corresponding to 70% of the theoretical yield.

EXAMPLE 5

To a solution of 1,8-heptadecadiene (23.3 g, purity 90% by weight, 89 mmol) in diphenyl ether (236 g) were added, at room temperature, 50.6 mg (81 µmol) of the metathesis catalyst of the formula IV. The reaction mixture was heated to 85° C. under reduced pressure (8 mbar). The cycloheptene product formed and other low boilers (for example 1-decene) were distilled homogeneously into a receiver during the reaction. After a reaction time of 24 h, a conversion of the reactant of >95% was found by means of GC analysis. The distillate comprised, according to GC analysis, an amount of 1.78 g (19 mmol) of cycloheptene, corresponding to 20% of the theoretical yield. After addition of a further portion of the metathesis catalyst (50 mg, 80 µmol), the reaction was continued for a further 6 h. Only traces of additional cycloheptene could then be detected in the receiver.

EXAMPLE 6

To a solution of 1,8-heptadecadiene (2.12 g, purity 90% by weight, 8 mmol) in diphenyl ether (21 g) were added, at 85° C., 2.56 mg (4 µmol, from standard solution) of the metathesis catalyst of the formula IV. After a reaction time of 3 h, the reaction mixture was analyzed. The reactant had been 88% converted and the reaction mixture comprised 110 mg (1 mmol) of cycloheptene, corresponding to 15% of the theoretical yield.

The invention claimed is:

1. A process for preparing cycloheptene, the process comprising:
ring-closing metathesis of 1,8-dienes of the formula I,

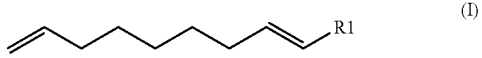

(I)

conducted in the presence of a catalyst,
where R1 is an alkyl group having 8 carbon atoms,
wherein the ring-closing metathesis is performed in a reaction mixture in the presence of in inert solvent, wherein the inert solvent is at least one solvent selected from the group consisting of a high-boiling aromatic hydrocarbon, halongenated hydrocarbon, and halogenated aromatic compound, and
the process further comprises removing cycloheptene by distillation from the reaction mixture and isolating cycloheptene, and metering into the reaction mixture the 1,8-diene of the formula I such that the concentration of the 1,8-diene of the formula I in the reaction mixture does not exceed 1 mol/l,
wherein the process is a continuous process.

2. The process according to claim 1, wherein the 1,8-diene of the formula I is initially charged in the reaction mixture in a concentration not exceeding 2 mol/l and the cycloheptene is removed from the reaction mixture by distillation and isolated during the reaction.

3. The process according to claim 1, wherein the reaction mixture additionally comprises an entraining agent.

4. The process according to any of claim 1, wherein a ruthenium-carbene complex is used as a catalyst for the ring-closing metathesis.

5. The process according to any of claim 1, wherein the olefin of the formula V formed in addition to the cycloheptene in the ring-closing metathesis of the 1,8-diene of the formula I

(V)

and/or the dimerization product thereof, the olefin of the formula VI

(VI)

is isolated as a coproduct of the process.

6. The process according to any of claims 1, wherein the 1,8-diene of the formula I is prepared by catalytic decarbonylation or oxidative decarboxylation of a carboxylic acid or of a carboxylic acid derivative of the formula VII,

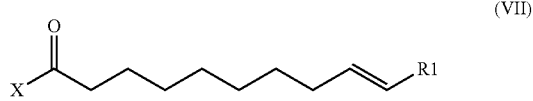

(VII)

wherein X is a leaving group and R1 is an alkyl group having 8 carbon atoms.

7. The process according to claim 6, wherein the leaving group X is selected from the group consisting of hydrogen atom, halide, an OH group, and an acyl group.

8. The process according to any of claim 1, wherein the 1,8-diene of the formula I or is purified before use in the ring-closing metathesis reaction.

9. The process according to any of claim 6, wherein the carboxylic acid or carboxylic acid derivative of the formula VII is oleic acid or an oleic acid derivative.

10. The process of claim 1, wherein the inert solvent is a high-boiling aromatic hydrocarbon selected from the group consisting of xylene, toluene, and cymene.

11. The process of claim 1, wherein the inert solvent is a halogenated hydrocarbon selected from the group consisting of dichloromethane and dichloroethene.

12. The process of claim 1, wherein the inert solvent is a halogenated aromatic compound selected from the group consisting of a dichlorobenzene and diphenyl ether.

13. The process of claim 1, wherein the catalyst is a Ru catalyst.

14. A process for preparing a cycloheptene, the process comprising:
ring-closing metathesis of a 1,8-diene of the formula I

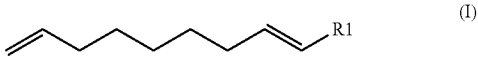

(I)

conducted in the presence of a catalyst,
wherein R1 is an alkyl group having 8 carbon atoms, wherein the ring-closing metathesis is performed in a reaction mixture in the presence of an inert solvent, wherein the inert solvent is at least one solvent selected from the group consisting of a high-boiling aromatic hydrocarbons, halogenated hydrocarbon, and halogenated aromatic compound, and the process further comprises removing cycloheptene by distillation from the reaction mixture and isolating cycloheptene, and metering into the reaction mixture the 1,8-diene of the formula I such that the concentration of the 1,8-diene of the formula I in the reaction mixture does not exceed 1 mol/l, wherein the ring-closing metathesis is conducted in the presence of a catalyst, and wherein the catalyst is a homogenous or heterogeneous metathesis catalyst of Re, Mo, or W.

15. The process of claim 1, wherein the inert solvent is at least one solvent selected from the group consisting of a high-boiling aromatic hydrocarbon and halogenated aromatic compound.

\* \* \* \* \*